(12) United States Patent
Juola et al.

(10) Patent No.: US 9,530,049 B2
(45) Date of Patent: Dec. 27, 2016

(54) KINETIC-BASED TOOL FOR BIOMETRIC IDENTIFICATION, VERIFICATION, VALIDATION AND PROFILING

(71) Applicant: DUQUESNE UNIVERSITY OF THE HOLY SPIRIT, Pittsburgh, PA (US)

(72) Inventors: Patrick Juola, Pittsburgh, PA (US); Michael Ryan, Pittsburgh, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 0 days.

(21) Appl. No.: 14/412,908

(22) PCT Filed: Jul. 9, 2013

(86) PCT No.: PCT/US2013/049676
§ 371 (c)(1),
(2) Date: Jan. 5, 2015

(87) PCT Pub. No.: WO2014/011608
PCT Pub. Date: Jan. 16, 2014

(65) Prior Publication Data
US 2015/0193653 A1    Jul. 9, 2015

Related U.S. Application Data

(60) Provisional application No. 61/670,556, filed on Jul. 11, 2012.

(51) Int. Cl.
*G06K 9/00* (2006.01)
*A61B 5/117* (2016.01)

(52) U.S. Cl.
CPC .......... *G06K 9/00342* (2013.01); *A61B 5/117* (2013.01); *A61B 5/1172* (2013.01); *G06K 9/00335* (2013.01); *G06K 9/00348* (2013.01)

(58) Field of Classification Search
None
See application file for complete search history.

(56) References Cited

U.S. PATENT DOCUMENTS 8,626,472 B2 * 1/2014 Solinsky ................ A61B 5/112
235/105
9,152,886 B2 * 10/2015 Sakai ................. G06K 9/00288
2008/0296851 A1 * 12/2008 Hall ....................... B62B 5/068
280/1.5

FOREIGN PATENT DOCUMENTS

JP    2004-310207    *    4/2004

\* cited by examiner

*Primary Examiner* — Shefali Goradia
(74) *Attorney, Agent, or Firm* — Barbara E. Johnson, Esq.

(57) ABSTRACT

A method for identifying an animal or human, including the steps of collecting and retaining an archive data set of measurements of two or more kinetic stylometrics of a first individual animal or human; collecting and retaining a test data set of measurements of the same two or more kinetic stylometrics of a test individual; and comparing archive and test data sets to determine similarity therefore, wherein similarity within any appropriate confidence interval confirms that the test individual and the first individual are the same. Using similar methods, social or other groups maybe kinetically stylometrically profiled for subsequent individual testing.

9 Claims, No Drawings

KINETIC-BASED TOOL FOR BIOMETRIC IDENTIFICATION, VERIFICATION, VALIDATION AND PROFILING

BACKGROUND OF THE INVENTION

1. Field of the Invention

The invention pertains to verifying identity with individual kinetics-based biometrics, and to profiling groups and individuals using the same technology.

2. Description of Related Art

Individual people may be recognized—and their identity verified—by a wide variety of methods at this writing. Government-issued credentials containing photographic identification are ubiquitous, and many biometric approaches for identifying individuals, not limited to fingerprints and retinal scans, are already known. Authorship technologies are available which determine the author of a writing based on stylometrics in the writing itself. More traditionally, and even in literature, certain biometrics were known for identity verification. For example, in *The Three Musketeers*, by Alexandre Dumas, a passage reads, "He entered the apartment followed by a man in a mask," and "[h]e was masked likewise; but I knew his step, I knew his voice, I knew him by that imposing bearing which hell has bestowed upon his person for the curse of humanity." In every day life, as well as in literature, people are frequently recognized by their voices, and by the sound of the way they walk, in addition to the way they look considered in a static fashion. In other words, sonic identity of voice or step is dynamic, and viewed within a time frame, but up until the present invention visual identification of a person has typically been accomplished in a static paradigm, with comparison of the subject with a still photograph, a static retinal scan, or an archived fingerprint taken at a single moment in time. To the inventors' knowledge, heretofore the technology has not existed to identify or to verify (or to profile) one or more individuals primarily or solely by their dynamic visuals or kinetics, that is, the kinetics or appearance of motion of the body and body parts including but not limited to the face, legs, arms and torso. Also to the inventors' knowledge, no one heretofore has even recognized the importance of the need to be able to identify and verify one or more individuals by their visible or kinetic characteristics in a dynamic system. For example, modern imaging including but not limited to satellite photography makes it much more feasible to assess dynamic visual images at a great distance, whereas sounds ("his step . . . his voice") can be heard only within much shorter ranges. A need therefore remains for a kinetic-based tool for identification in which the way a person moves becomes as much a verification technology of who he or she is as would a fingerprint, retinal scan or authorship stylometric.

SUMMARY OF THE INVENTION

In order to meet this need, an archive data (AD) set of kinetic stylometrics of an individual human being or animal is created by assessing and recording at least two, preferably at least three, more preferably at least five and most preferably at least ten kinetic stylometrics of the individual and recording the data. The kinetic stylometrics may be selected from a wide variety of typical body movements such as average speed of walking; extent and velocity of arm swinging during walking; crest and trough values of vertical walking arc measured at the hip; stride length; crest and trough values of vertical walking arc measured at the head; extent, velocity or rotation of movements while standing predominantly still; extent and velocity of spinal extension off-center when walking or standing; and extent and velocity of shoulder roll (side-to-side) while walking or standing, etc. The kinetic stylometrics are measured either by a physical sensor, such as is carried on the person of the individual, or by video capture, or both. Mathematically, whether the two, three, five, ten or more kinetic stylometrics are similar enough to a single individual to confirm the identity of an individual may be determined by various mathematic comparisons that assess confidence interval, such that the present invention is able to confirm the identity of an individual by his or her kinetic stylometrics when test data (TD) for a test individual is similar to archive data for a known individual within any appropriate confidence such as 90%, preferably 95%.

DETAILED DESCRIPTION OF THE INVENTION

The present invention is a system for identifying an individual based upon between two to ten or more typical kinetic stylometrics of an individual, that is, the unique ways the person typically moves. Ordinarily, a kinetic profile of an individual human being or animal is created by assessing and recording at least two, preferably at least three, more preferably at least five and most preferably at least ten kinetic stylometrics of the individual. Typically such a set of archive data is stored in a computer with attribution of the data to the individual. The kinetic stylometrics may be selected from a wide variety of typical body movements such as average speed of walking; extent and velocity of arm swinging during walking; crest and trough values of vertical walking arc measured at the hip; stride length; crest and trough values of vertical walking arc measured at the head; extent, velocity or rotation of movements while standing predominantly still; extent and velocity of spinal extension off-center when walking or standing; and extent and velocity of shoulder roll (side-to-side) while walking or standing, etc. The kinetic stylometrics are measured either by a physical sensor, such as is carried on the person of the individual, or by video capture, or both. Measured data is typically stored in the memory of a computer. Mathematically, whether the two, three, five, ten or more kinetic stylometrics are similar enough to a single individual to confirm the identity of an individual may be determined by various mathematic comparisons that assess confidence interval, such that the present invention is able to confirm the identity of an individual by his or her kinetic stylometrics when test data for a test individual is similar to archive data for a known individual within any appropriate confidence interval, such as greater than 90%, preferably greater than 95%.

From start to finish, then, the present technology embraces measuring from two to ten or more kinetic stylometrics of an individual (human or animal) and recording the data thus measured, typically followed by archiving such data in a computer having an output to a user to create an archive data set. In order to identify or verify an individual for whom archive data has already been collected, between two to ten or more kinetic stylometrics of the individual are measured using kinetics sensors, video measurement or both to create a test data set. The test data set and the archive data set are then compared, typically by a computer algorithm implementing mathematical comparison, to assess the similarity of the test data and the archive data. Test data stylometrics actually collected are then compared only to the corresponding stylometric data available in the archive data set. The realization of the mathematical comparison is not limited to a single algorithm, but may be accomplished by any known mathematical comparison that computes and reports data similarity within stated confidence thresholds. When the test data set and the archive data set are compared in the computer in which the archive data was stored (or in an intercommunicating computer associated therewith) as to the individual for whom identity is to be verified, a 90% confidence interval as to the similarity of the archive data set and the test data set—preferably, a 95% confidence interval—verifies that the individual being tested has the identity of the individual for whom the archive data was previously stored.

As with any instance pertaining to kinetics, time considerations are key. First of all, the preparation of an archive data set for a given individual does not have to happen very much in advance of the testing of an individual human or animal for identity verification. In fact, the time lapse might be measured in as little as seconds or fractions of seconds, such as would occur in a facility in which initial entrance requires presentation of traditional photographic or other credentials while at the same time an initial archive data set of kinetic stylometrics is compiled for the same individual. After such initial creation of an archive data set, video monitoring throughout the facility can continue to confirm the identity of the same individual based only on his or her motions—and can do so starting in as small a time period as a few seconds or fractions of a second after completion of the archive data set. By the way, ideally any archive data set for an individual is collected without the knowledge of the individual, such as video monitoring over a, say, five-minute period including the individual's walking approach to a locus for identity verification such as a guard station or customs gate, among others, followed by standing and conversing and then followed by more walking, all with customary associated natural subsidiary movements. Capturing the archive data set without the knowledge of the individual reduces or eliminates the possibility of posturing by the individual to create a misleading data set (or to try to emulate the archive data set of another). Having said that, however, two or more kinetic stylometrics are virtually impossible consciously to alter in the short term with any consistency, because human subjects cannot convincingly modify even a single kinetic stylometric without extensive retraining. As an illustrative example, consider a person's trying to change the crest and trough values of the vertical walking arc measured at the hip. It is conceivable that over a period of training, a person wishing to mask earlier walking arc crest/trough data (or to emulate someone else's) could retrain him- or herself to a different crest/trough stylometric, but doing so would take repetitive practice and determination in order to institute a new, consistent habit. By contrast, within an hour or a day it would be virtually impossible for an individual to change walking arc crest/trough data with any consistency, and any inconsistent kinetic stylometric data for a test individual is an immediate indication that the individual is an imposter. The likelihood that a given individual could posture or alter two separate kinetic stylometrics within a period of a day or less is therefore extremely low. Preferably according to the invention, therefore, the present invention is implemented using archive data sets created as recently as possible for use to compare with the test data sets, and most preferably but by no means necessarily the archive data sets are created within 24 hours of use.

As further considerations of time and timing, typically both the archive data sets and the test data sets are created over a minimum of at least one minute of activity, preferably over at least five minutes of activity or more. When a period of five minutes of combined sitting, standing or walking (as are applicable during those five minutes) are analyzed all together, the likelihood of uncovering inconsistencies indicative of posturing are greatly increased. One of the internal security aspects of the present invention is that two or more kinetic stylometrics are chosen and analyzed. Even professional actors, who are more adept at overall physical mimicry than any trained intelligence agent or other imposter could ever be, can only mimic physical behavior according to the parameters they perceive and emulate, consciously or unconsciously. The present invention therefore acknowledges that, over time, the choice of which two or more stylometrics are assessed becomes important, because as individuals might try to affect or mask their, say, stride length or shoulder roll depth, the practice of the invention allows choice of different kinetic stylometrics, such as (say) average degree of elbow bending upon flexion, or eye blink duration and periodicity. In the most preferred embodiment of the invention, assessing and comparing ten or more kinetic stylometrics provides a virtually uncrackable identification system, because even the most adept life-long professional actors cannot reschool themselves to alter permanently ten kinetic stylometrics with consistency over any given five-minute or greater time period during which they might otherwise without notice be observed.

As may be seen from the immediately previous description, a high confidence interval match of a test individual's kinetic stylometrics test data set with an archive data set is extremely difficult if not impossible to forge. Compared to the possibility of forgery of paper or photographic credentials, even those containing embedded electronics, the likelihood of forgery of a kinetic stylometric identification according to the present invention is relatively much lower. Even so, kinetic stylometrics according to the present invention may be used as adjunct identification and verification technology to accompany other identity verification methods.

Another important aspect of the invention inheres in the recognition that, while any given individual's kinetic stylometrics will be unique, there are indeed groups for which some kinetic stylometric similarity is apparent. For example, a husband and wife married for twenty years will exhibit more kinetic stylometric similarities than will two random individuals who have never met, due to long-recognized conformity of habits and mannerisms over time typically attributable to married couples. Other social groups also contain individuals whose kinetic stylometrics are overall more similar than would occur in the same size group of individuals randomly chosen. Some of the kinetic stylometric similarities in social groups have nothing to do with the most common behavior stereotypes that may be anecdotally associated with those groups, and in any case the creation of the archive data set is empirical and objective. By preparing kinetic stylometrics archive data sets for populations, as well as individuals, and by calculating common similarities of stylometrics for the population, it is then possible with the present invention to profile an individual's kinetic stylometrics test data to profile whether the individual has a likely attribution to the given population. "Profiling" does not by any means need to be considered as a pejorative word, or concept—distasteful, immoral or illegal behavior might result from how profiling is used, but not from the fact that it is performed. Profiling can also have extremely positive application in identifying an individual, such as without limitation by confirming, using video monitoring, the likely participation in a large sorority or fraternity event of only alumni of the sorority or fraternity, and not outsiders including criminals or terrorists or even simply imposters or poseurs.

By analogy to authorship attribution, the present invention typically embraces a "distractorless" comparison of an individual's test data to an archive data set attributable to the same purported individual. It is within the scope of the invention, however, to use archive "distractor sets" of kinetic stylometric data deliberately attributable to one or more individuals other than the individual whose identity is desired to be confirmed, to provide a basis of comparison. Mathematically, the algorithm does not change appreciably when comparing test data to archive data—if distractor sets are used, then multiple comparisons are made, and the confirmation of purported identity is confirmed in part by dissimilarity of the test data to the distractor set archive data.

A typical algorithm suitable for use in the present invention is AD=<a, b, c, d, e, f, g, h, i, j>, for ten kinetic stylometrics, where a through j each represents a single kinetic stylometric measured, if applicable, over a stated time, and where AD is a ten-dimensional vector of "archive data." If TD (test data)=<a', b', c', d', e', f', g', h', i', j'>, and points AD and TD are sufficiently close in ten-dimensional space (or alternatively, if the cosine of the angle in ten-dimensional space between AD and TD is sufficiently small), the individual associated with TD is verified to be the individual whose archive data AD was used for comparison. In this case, "sufficiently close" and "sufficiently small" can mean "within a 90%, preferably 95%, confidence interval of zero." For iterations using fewer than or more than ten kinetic stylometrics, decrease or increase a through j accordingly. Comparing two or more kinetic stylometrics of a test individual to an archive individual is not mathematically difficult—knowing to do so, however, is the basis of the present invention. Assigning numeric values to each of a, b etc. should be accomplished as follows. For any given kinetic stylometric a, b, etc., use consistent parameters for AD and TD. For example, if hip-height crest and hip-height trough are measured as absolute values, use absolute values for both AD and TD. However, if hip-height crest to trough is measured as a differential, use the differential for both AD and TD. Any measurements that are made over time should be made over the same time increment in both AD and TD. When absolute vertical measurements are used, subtract shoe heel height. Video measurements should be corrected for parallax (see below). One skilled in the art can quantify kinetic stylometrics after learning from this specification the benefit of doing so, and of comparing AD to TD to determine extent of similarity. The most important aspect of the algorithm is to include as a, b, etc. only a parameter for which a meaningful datum was measured—in other words, reflexive repetitive yawning or stretching could be included as a kinetic stylometric, but an isolated instance of yawning due to fatigue would not. As to other practical applications distinct from the present invention, the ten dimensional mathematical approach to similarity calculations described above has already been established at this writing—see for example: Chen, Yihua, et al., (2009), Similarity-based Classification: Concepts and Algorithms, *Journal of Machine Learning Research,* 10 747-776; Kumar, Sushanta, et al. (2011), Similarity Analysis of Legal Judgements, *COMPUTE* '11, March 26-26, Bangalore, Karnataka, India; Juola, Patrick. (2006), Authorship Attribution, *Foundations and Trends in Information Retrieval,* 1(3) 233-334; Guo, Xin, (2011), A vector space model approach to social relation extraction from text corpus, *Fuzzy Systems and Knowledge Discovery (FSKD),* 3 1756-1759; Binongo, Jose Nilo G., (2003), Who Wrote the 15th Book of Oz? An Application of Multivariate Analysis to Authorship Attribution, *Chance,* 16(2) Spring 2003; and Manning, Christopher D. and Hinrich Schütze, (1999), *Foundations of Statistical Natural Language Processing,* Cambridge, MIT Press.

The invention embraces any form of measurement of kinetic stylometrics, and particularly the two techniques of the carried one-or-more motion sensors and, separately, video measurement of moving images of body parts. Sensors are already known at this writing that can measure movement—perhaps the best known of these is the predominant motion sensor found in a pedometer. Motion, altitude and rotation sensors of any type are embraced by the invention—and the individual may carry two or more sensors specific to the kinetic stylometric to be measured. At this writing a typical sensor might weight about a gram, so even carrying one hundred sensors, at a mere 100 grams, is tenable in the practice of the invention—particularly if the sensors are distributed among clothing (different areas), shoes, eyeglasses, accessories, personal electronic devices and hats or headgear. Alternatively, video monitoring and measurement of kinetic stylometrics may be made in a direct and intuitive fashion. However, for video measurement and in accommodation of parallax, length or width movement measurements should be made as a percentage of height or width of the individual, rather than as absolute measurements, to permit correct comparison of TD to AD (angle, rotation, and time repetitions are independent of parallax). As long as the units for a, b, etc are consistent, summation and comparison of the kinetic stylometrics enables the determination of similarity within a confidence level directly provided by the extent of similarity.

Additional possible kinetic stylometrics include, without limitation: swallowing periodicity; reflexive grimacing arc or periodicity; extent and speed of fingernail tapping; seated leg-shaking or foot-tapping speed and percentage of incidence; instances of lip-licking per unit time, and frequency thereof; incidence and frequency of apparent solo vocalization as assessed by lip-reading or visualization only; chair adjustment extent and frequency when seated; speed and orientation of leg-crossing; incidence and frequency of head-nodding while conversing; incidence and frequency of head-nodding while listening; side-to-side head shaking periodicity; extent of reflexive coverage of the mouth with the hand and frequency of repetition; extent of reflexive coverage of the forehead or eyes with the hand and frequency thereof; time elapsed between visible sighs; time elapsed between raised-arm stretches or yawns; or time elapsed between "eye rolls." Part of the elegance of the present invention is that, in either the archive data set or the test data set, any parameter for which there is no consistent value—such as an isolated yawn or eye-roll, not a habitual behavior—is simply eliminated from consideration at all. The comparison of similarity of TD to AD thus a priori provisionally imputes to the test individual the habitual behaviors in the archive data, and failure to confirm with the habitual behaviors tends to show that the test individual does not match the identify for the individual for whom the archive data set was made. In any case, the endless possibility of kinetic stylometrics—and the ability within the scope of the invention for the practitioner to change the choice of stylometrics archived and compared—means that a potential imposter can never be sure of which kinetic stylometrics to attempt to emulate and therefore can virtually always be thwarted as to identity forgery attempts. From the standpoint of national security, then, the ability constantly to change the choice of which kinetic stylometrics to track, if any, keeps any potentially malicious perpetrators from knowing whether or which of their typical movements might be under scrutiny, if any at all. In other words, the ability to implement the present invention not only without an individual's knowing it—by using video assessment for example,—but also the inability of an individual to second-guess the present system even once it is known, means that the present invention can be used to identify or profile terrorists, for instance, and yet even if the purported terrorist knows about the present invention he or she gains no strategic benefit that the invention itself cannot intrinsically overcome simply be reassigning different, maybe even randomly-chosen, kinetic stylometrics to the equation for evaluation.

Although the invention has been described very particularly above, with mention of particular parameters and examples, the invention is only to be limited insofar as is set forth in the accompanying claims.

The invention claimed is:

1. A method for identifying, verifying, validating or profiling an animal or human or groups thereof, comprising the steps of: collecting an archive data set (AD) consisting of measurements of at least ten unique body movement kinetic stylometrics of a first individual animal or human and retaining said archive data set in a computer having an output to a user; collecting a test data set (TD) of measurements of the same at least ten unique body movement kinetic stylometrics of a test individual animal or human who is the same as or different than said first individual animal or human and retaining said test data set in a computer having an output to a user; and comparing said archive data set and said test data set, with similarity between the test data set and the archive data set indicating that the first individual and the test individual are the same, and with the comparison calculation rendered as an output to a user.

2. The method according to claim 1, wherein said body movement kinetic stylometrics are selected from the group consisting of average speed of walking; extent and velocity of arm swinging during walking; crest and trough values of vertical walking arc measured at the hip; average stride length; crest and trough values of vertical walking arc measured at the head; extent, velocity or rotation of repetitive movements while standing predominantly still; extent and velocity of spinal extension off-center when walking or standing; extent and velocity of shoulder roll (side-to-side) while walking or standing; swallowing periodicity; reflexive grimacing arc or periodicity; extent and speed of fingernail tapping; seated leg-shaking or foot-tapping speed and percentage-of-time of incidence; instances of lip-licking per unit time and frequency thereof; incidence and frequency of apparent solo vocalization as assessed by lip-reading or visualization only; chair adjustment extent and frequency when seated; speed and orientation of leg-crossing; incidence and frequency of head-nodding while conversing; incidence and frequency of head-nodding while listening; side-to-side head shaking periodicity; extent of reflexive coverage of the mouth with the hand and frequency of repetition; extent of reflexive coverage of the forehead or eyes with the hand and frequency thereof; time elapsed between visible sighs; time elapsed between raised-arm stretches or yawns; time elapsed between eye rolls; and periodicity and technique of scratching the head, nose or ears.

3. The method according to claim 1, wherein said archive data (AD) set and said test data (TD) set are further compared to at least one distractor data (DD) set comprised of body movement data collected from one or more individuals other than either the first individual or the test individual.

4. A method for identifying, verifying, validating or profiling an animal or human or groups thereof, comprising the steps of: collecting an archive data set (AD) consisting of measurements of two or more body movement kinetic stylometrics of a first individual animal or human and retaining said archive data set in a computer having an output to a user; collecting a test data set (TD) of measurements of the same two or more body movement kinetic stylometrics of a test individual animal or human who is the same as or different than said first individual animal or human and retaining said test data set in a computer having an output to a user; and comparing said archive data set and said test data set, with similarity between the test data set and the archive data set indicating that the first individual and the test individual are the same, and with the comparison calculation rendered as an output to a user, wherein said archive data (AD) set and said test data (TD) set are further compared to at least two or more distractor data (DD) sets comprised of body movement data collected from two or more individuals belonging to a definable group for the purpose of creating a profile of said definable group and determining whether the test individual belongs to said definable group.

5. The method according to claim 1, wherein the computer calculates the data and provides the results as an output for a user where AD=<a, b, c, d, e, f, g, h, i, j>, for ten kinetic stylometrics, where a through j each represents a single body movement kinetic stylometric measured and where AD is a ten-dimensional vector, and wherein the computer compares AD to TD (test data)=<a', b', c', d', e', f, g', h', j'>, such that if points AD and TD are sufficiently close in ten-dimensional space, or if the cosine of the angle in ten-dimensional space between AD and TD is sufficiently small, the individual associated with TD is verified to be the individual whose archive data AD was used for comparison.

6. The method according to claim 5, wherein when TD=AD with a confidence interval of 90%, said test individual and said first individual are the same.

7. The method according to claim 6, wherein TD and AD are each collected over a period of time of one minute.

8. The method according to claim 6, wherein TD and AD are each collected over a period of time of five minutes.

9. The method according to claim 5, wherein when TD=AD with a confidence interval of 95%, said test individual and said first individual are the same.

* * * * *